United States Patent
Singh et al.

(10) Patent No.: US 12,027,246 B1
(45) Date of Patent: Jul. 2, 2024

(54) APPARATUS, SYSTEM AND METHOD FOR PROCESSING MEDICAL DATA IN A COMPUTER SYSTEM

(71) Applicant: ALLSCRIPTS SOFTWARE, LLC, Chicago, IL (US)

(72) Inventors: Ankit Singh, Apex, NC (US); Ethan O'Brien, Raleigh, NC (US)

(73) Assignee: Allscripts Software, LLC, Chicago, IL (US)

( * ) Notice: Subject to any disclaimer, the term of this patent is extended or adjusted under 35 U.S.C. 154(b) by 287 days.

(21) Appl. No.: 16/507,940

(22) Filed: Jul. 10, 2019

(51) Int. Cl.
*G16H 10/60* (2018.01)
*G16H 10/40* (2018.01)
*G16H 20/00* (2018.01)
*G16H 20/13* (2018.01)
*G16H 10/20* (2018.01)
*G16H 15/00* (2018.01)
*G16H 70/20* (2018.01)

(52) U.S. Cl.
CPC ............ *G16H 20/13* (2018.01); *G16H 10/40* (2018.01); *G16H 10/60* (2018.01); *G16H 20/00* (2018.01); *G16H 10/20* (2018.01); *G16H 15/00* (2018.01); *G16H 70/20* (2018.01)

(58) Field of Classification Search
CPC ........ G16H 10/00–80/00; G16H 10/20; G16H 10/40; G16H 10/60; G16H 20/00; G16H 15/00; G16H 70/20; G06F 1/00–2221/00; G06Q 10/00–2250/00
USPC .......................................................... 705/2
See application file for complete search history.

(56) References Cited

U.S. PATENT DOCUMENTS

| 2013/0198207 A1* | 8/2013 | Dolan | G06F 16/245 707/749 |
| 2016/0110512 A1* | 4/2016 | Adjaoute | G06Q 10/10 705/2 |

(Continued)

FOREIGN PATENT DOCUMENTS

WO WO-2019126363 A1 * 6/2019 ....... G01N 33/48792

OTHER PUBLICATIONS

K. Miller and G. Mansingh, "Towards a distributed mobile agent decision support system for optimal patient drug prescription," Third International Conference on Innovative Computing Technology (INTECH 2013), 2013, pp. 233-238, doi: 10.1109/INTECH.2013.6653659. (Year: 2013).*

(Continued)

*Primary Examiner* — Jason B Dunham
*Assistant Examiner* — Nicholas Akogyeram, II
(74) *Attorney, Agent, or Firm* — Peter Zura; LOZA & LOZA, LLP

(57) ABSTRACT

Technologies and techniques for processing drug data in a specialized medical computer system. Autonomous moving code may be received via a communications interface from a computer network, where the autonomous movable code includes patient data, lab test data, demographic data, and diagnosis data. The autonomous movable code is executed in a system agent manager and processed in a learning module, where the learning module performs predictive processing to determine if an opioid abuse condition exists. New autonomous movable code may be generated that includes information and/or instructions regarding the opioid abuse condition. The new autonomous movable code is then transmitted back to the computer network.

20 Claims, 7 Drawing Sheets

(56) References Cited

U.S. PATENT DOCUMENTS

2018/0174673 A1\* 6/2018 DeFrank ............... G16H 80/00
2019/0198142 A1\* 6/2019 Lu ......................... G16H 20/10

OTHER PUBLICATIONS

Aditya V. Karhade, et al. "Development of machine learning algorithms for prediction of prolonged opioid prescription after surgery for lumbar disc herniation", The Spine Journal, vol. 19, Issue 11. Available online Jun. 9, 2019. 2019, (Year: 2019).\*

G. Zhang et al., "A sparse Bayesian multi-instance multi-label model for skin biopsy image analysis," 2013 IEEE International Conference on Bioinformatics and Biomedicine, 2013, pp. 261-266, doi: 10.1109/BIBM.2013.6732500. (Year: 2013).\*

Kevin Miller & Gunjan Mansingh, Towards a distributed mobile agent decision support system for Optimal Patient Drug Prescription, Third International Conference on Innovative Computing Technology (INTECH 2013), 233-238 (2013) (Year: 2013).\*

Georgiy Bobashev et al., Pain town, an agent-based model of opioid use trajectories in a small community, Social, Cultural, and Behavioral Modeling, 274-285 (2018) (Year: 2018).\*

\* cited by examiner

| Opioid ID | Opioid Name | Symptoms List | Duration | Characteristics |
|---|---|---|---|---|
| 1 | Morphine | Dizziness, nausea | 2 months | Low physical activity, laziness |
| 11 | Hydrocodone | Body aches, laziness | 3 weeks | Social withdrawal, depression |
| 23 | Methadone | Fever, dizziness | 5 days | Lethargy, speech slur |
| 43 | Buprenorphine | Nausea, body ache, migraine | 3 months | Emotional distress, irregular heartrate |
| 15 | Oxycodone | Migraine, nausea, stomach ulcers | 10 days | Low physical activity, fatigue |

*FIG. 6*

| Opioid ID | Patient ID | Patient Name |
|---|---|---|
| 15 | A3D969C5-6E90-44F0-9DE9-3E5201125321 | Doe, Jane |
| 11 | A6FF25AE-FBD4-4AB1-8FF1-C18D753D5C3F | Doe, Jane |
| 42 | 46490700-C07F-4707-A4B2-B495D06AB6E8 | Public, John Q. |

*FIG. 7*

APPARATUS, SYSTEM AND METHOD FOR PROCESSING MEDICAL DATA IN A COMPUTER SYSTEM

FIELD OF TECHNOLOGY

The present disclosure is directed to technologies and techniques for processing medical data in a computer system. More specifically, the present disclosure is directed to predictive processing and distributed computer processing for medical computer systems utilizing Electronic Health Records (EHR) and/or Electronic Medical Records (EMR).

BACKGROUND

Medical software technology has advanced through the years to allow health care providers to monitor and improve the health care services provided to patients. Unlike conventional generic software systems, medical software technology must be specifically configured to process medical codes and provide ample security for patient data. Practice management software (PM) has been developed to manage different administrative and clinical aspects of healthcare. This software centralizes various systems so users can run things more efficiently. It automates almost every task that fits under the "health information management" umbrella.

Electronic medical record (EMR) systems are one of the most commonly-used medical software categories. EMRs replaced paper records by digitizing medical charting, making digital versions of charts and patient histories. These systems can also create alerts when patients are due for preventive procedures and screenings. In addition, EMRs help physicians treat patients by looking at their history and comparing their health data against past entries. Electronic health record (EHR) systems function similarly to EMRs, though the former is a more robust system overall. EHRs allow users to review a patient's history, diagnoses, treatments, medications, allergies, X-rays, test results and more. One difference between EMRs and EHRs is how information is shared by each. Data from EMRs can only be viewed within one office while EHRs can share patient data with other EHRs. If a patient moves, or goes to an emergency room, they can be properly treated because different physicians will have access to their information.

Patient portals help people view everything contained in an EMR and EHR, including patient history, treatments and medications. Users of patient portals can review records or additional notes, even when they aren't in an office. These systems have increased in popularity among hospitals and medical practices in recent years. E-prescribing, or electronic prescribing, as well as computerized physician order entry (CPOE) systems are technology frameworks that allows physicians and other medical practitioners to write and send prescriptions to a participating pharmacy electronically instead of using handwritten or faxed notes or calling in prescriptions.

Prescription monitoring programs (PMPs) or prescription drug monitoring programs (PDMPs) are state-run programs that collect and distribute data about the prescription and dispensation of federally controlled substances and other potentially addictive or abusable prescription drugs. PMPs help to prevent adverse drug-related events through opioid overdoses, drug diversion, and substance abuse by decreasing the amount and/or frequency of opioid prescribing. Pharmacies dispensing controlled substances and prescribers are typically required to register with their respective state PMPs and (for pharmacies and providers who dispense controlled substances from their offices) to report the dispensation of such prescriptions to an electronic online database.

Current PMP systems require special formatting for the data, and is often secured behind a server-centric system configuration. This often requires users to directly connect to a PMP server and/or database in order to obtain PMP data. Additionally, current PMP systems are often inefficient in identifying and predicting PMP data that anticipated a potential abuse condition. Further, conventional client-server computer platform configurations in a larger-scale medical setting may produce excessive network load, network latency, and is not optimally equipped to handle parallel processing, asynchronous execution, protocol encapsulation, dynamic adaptation, fault-tolerance and robustness.

SUMMARY

Various apparatus, systems and methods are disclosed herein relating to specialized computer systems for drug data processing.

In some illustrative embodiments, a system is disclosed for processing drug data in a computer network, comprising a processor; a memory, operatively coupled to the processor; a communications interface, operatively coupled to the processor, wherein the communications interface is configured to communicate with an electronic prescription application to receive prescription drug monitoring program (PDMP) data from the computer network, and receive autonomous movable code from the computer network, the autonomous movable code comprising at least one of patient data, lab test data, demographic data, and diagnosis data; a system agent manager, configured to execute the autonomous movable code; and a learning logic, configured to process the executed autonomous movable code and the PDMP data and, based on the processing, predictively determine if an opioid abuse condition exists, wherein the system agent manager is configured to generate new autonomous movable code comprising information on the opioid abuse condition and transmit the new autonomous movable code to the computer network via the communications interface.

In some illustrative embodiments, a method is disclosed for processing drug data in a computer network, comprising communicating, via a communications interface, with an electronic prescription application to receive prescription drug monitoring program (PDMP) data from the computer network; receiving, via the communications interface, autonomous movable code from the computer network, the autonomous movable code comprising at least one of patient data, lab test data, demographic data, and diagnosis data; executing, via a system agent manager, the autonomous movable code; and processing, via a learning logic, the executed autonomous movable code and the PDMP data and, based on the processing, predictively determining if an opioid abuse condition exists; and generating, via the system agent manager, new autonomous movable code comprising information on the opioid abuse condition and transmit the new autonomous movable code to the computer network via the communications interface.

In some illustrative embodiments, a method is disclosed for processing drug data in a computer network, comprising communicating, via a communications interface, with an electronic prescription application to receive prescription drug monitoring program (PDMP) data from the computer network; receiving, via the communications interface, autonomous movable code from the computer network by invoking, via a system agent manager, an Agent Management System (AMS) and Directory Facilitator (DF) to receive the autonomous movable code from the computer network, the autonomous movable code comprising at least one of patient data, lab test data, demographic data, and diagnosis data; executing, via the system agent manager, the autonomous movable code; and processing, via a learning logic, the executed autonomous movable code and the PDMP data and, based on the processing, predictively determining if an opioid abuse condition exists; and generating, via the system agent manager, new autonomous movable code comprising information on the opioid abuse condition and transmit the new autonomous movable code to the computer network via the communications interface.

BRIEF DESCRIPTION OF THE FIGURES

The present invention is illustrated by way of example and not limitation in the figures of the accompanying drawings, in which like references indicate similar elements and in which:

FIG. 6 shows simplified medical data comprising PDMP data configured for data mapping and for use in predictive data processing under an illustrative embodiment;

FIG. 7 shows a simplified processing table that identifies controlled drugs with a patient ID under an illustrative embodiment.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that the programming techniques and hardware arrangements disclosed herein, embodied on tangible mediums, are configured to transform the conventional hardware components into new machines that operate more efficiently (e.g., providing greater and/or more robust data, while using less processing overhead and/or power consumption) and/or provide improved user workspaces and/or toolbars for human-machine interaction.

Figure 1:
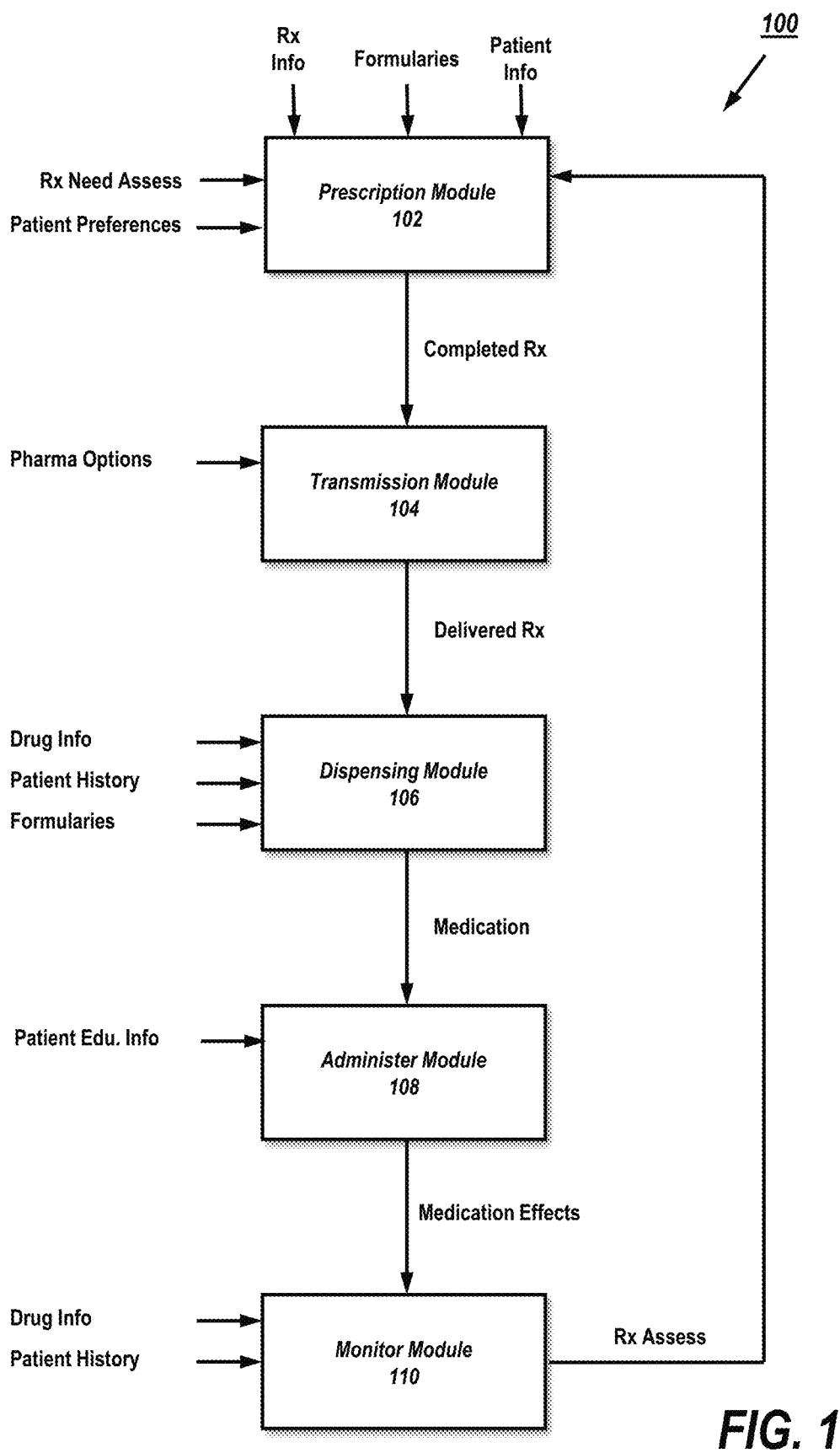
FIG. 1 illustrates a simplified block diagram of a processor-based computer system configured to perform medical data processing, functional modeling and medication management under an illustrative embodiment.

Turning to FIG. 1, the drawing illustrates a simplified block diagram of a processor-based computer system 100 configured to perform medical data processing, functional modeling and medication management under an illustrative embodiment. The computer system 100 may be embodied in a single server, or may be embodied among multiple servers, including a cloud network under some illustrative embodiments. The computer system may be configured using an electronic prescribing ("e-prescribing") platform, and may utilize function modeling methodologies, including functional modeling languages for the data analysis, development, reengineering, and integration of information systems, business processes; or software engineering analysis. In one example, the computer system 100 may utilize IDEF0 ("Icam DEFinition for Function Modeling"), where IDEF0 is part of the IDEF family of modeling languages in the field of software engineering, and is built on the functional modeling language Structured Analysis and Design Technique (SADT).

As is shown in the figure, prescription module 102 may be configured to receive or load as inputs medical data including, but not limited to, patient preferences, prescription need assessment, prescription information, formularies data, and patient information. The data for prescription module 102 may be provided by a prescribing clinician database, as well as components from an e-prescribing system. Prescription need assessment data comprises data relating to a clinician's assessments about the need for prescription medications. Data relating to the patient's preferences regarding medications as well as drug information, patient data (e.g., known allergies), and drug formulary restrictions, are also processed in prescription module 102. The output comprises a completed prescription, as shown in the figure and may also include output information instructing patient adherence to the prescribed regimen.

After processing this data, prescription module 102 provides a completed prescription to transmission module 104. Using pharmacy option data input that is entered and/or loaded, transmission module transmits delivered prescription data to dispensing module 106, which further process the data, along with data inputs including, but not limited to, drug information, patient history and formulary data. In some illustrative embodiments, problematic prescriptions may be identified in the dispensing module 106 using the techniques described herein, and may be changed or cancelled rather than being dispensed. The administer module 108 may include a patient education information data input as shown an outputs medication effects to monitor module 110, which may include a clinician input of drug information and patient history, where monitor module may output a prescription assessment that may be fed back to prescription module 102 for processing and use during subsequent prescription processes. It should be understood by those skilled in the art that the modules 102-110 of computer system 100 may be combined in various forms, depending on the application, and may include additional modules, depending on the specific application.

Figure 2:
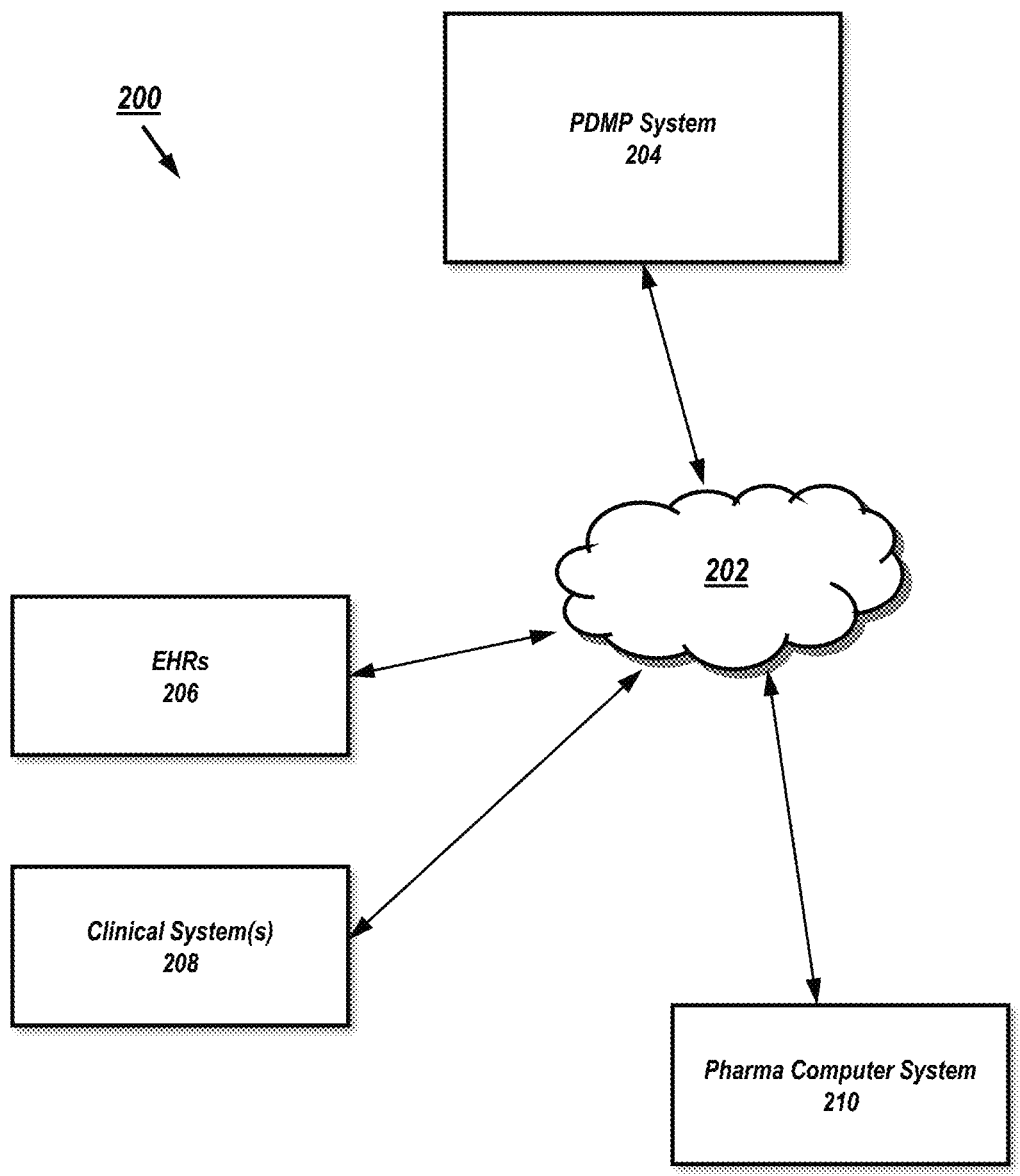
FIG. 2 shows a simplified block diagram of a Prescription Drug Monitoring Program (PDMP) computer system under an illustrative embodiment.

FIG. 2 shows a simplified block diagram of a Prescription Drug Monitoring Program (PDMP) network system 200 under an illustrative embodiment. In this example, a PDMP system 404 (e.g., PMP AWARxE) is communicatively coupled to a computer network 402, which in turn is communicatively coupled to Electronic Health Record (EHR) system 406, one or more clinical systems 408 and pharmacy computer system 410. In some illustrative embodiments, one or more portions of the PDMP network system 200 may be configured to operate under the U.S. Meds Prescription Drug Monitoring Program FHIR Implementation Guide (US Meds PDMP FHIR IG), where one or more portions of PDMP data may be accessed using the Health Level-7 Fast Healthcare Interoperability Resources (HL7 FHIR) standard. In some illustrative embodiments, other standards may be combined or substituted with the HL7 FHIR standard.

During operation, the one or more clinical systems 408 may obtain PDMP data for processing. Each clinical system 408 may comprise a plurality of devices configured to communicate with each other and with the network 402, as well as other devices that may be coupled to the PDMP network system 200. The one or more clinical systems 408 may obtain medical data comprising EHR data from EHR system 406, and may receive pharmaceutical data from pharmacy computer system 410. PDMP data may be obtained from PDMP system 404. In one example, a clinical system (408), using a suitable application (e.g., SMART, FHIR, etc.) may issue a PDMP request, requesting a patient's controlled substance history. In response, the PDMP system accepts the request and transmits a controlled substance history for the patient. The PDMP system 404 may comprise an intermediary system in some illustrative embodiments, where the intermediary system may communicate with a plurality of PDMP systems for obtaining PDMP data. The intermediary system may be configured within a specific system (e.g., clinical system 408), or may be configured as a stand-alone system.

Figure 3:
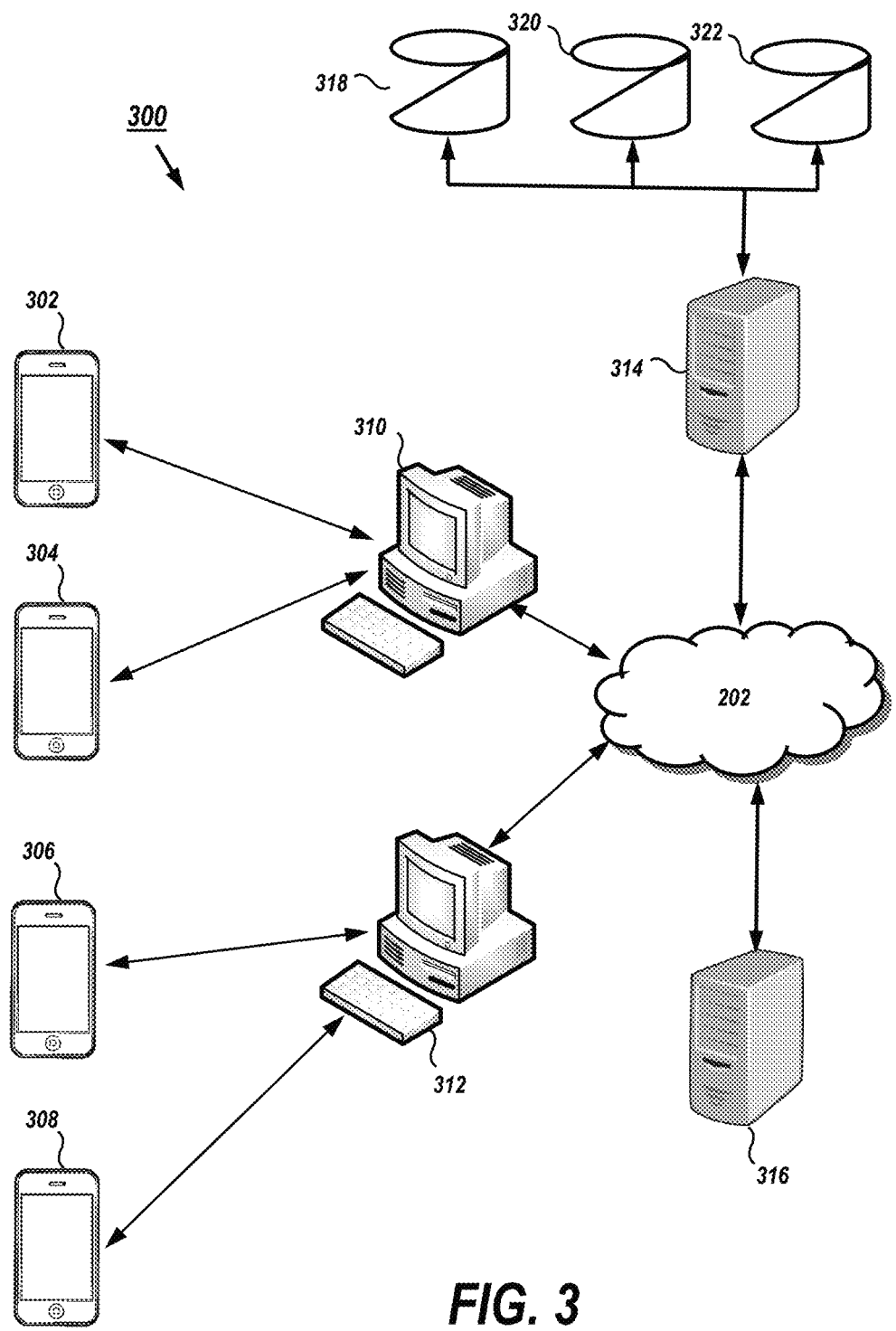
FIG. 3 illustrates a simplified overview of a processor-based computer system configured to perform medical data processing utilizing mobile agents under an illustrative embodiment.

FIG. 3 illustrates a simplified overview of a processor-based computer system 300 configured to perform medical data processing utilizing mobile agents under an illustrative embodiment. The system 300 may include a plurality of portable processing devices 302, 304, 306, 308 and associated computers and/or workstations 310, 312. Those skilled in the art understand that portable processing devices 302-308 and computers 310-312 may be configured as any suitable device that include, but are not limited to, cell phones, tablets, laptops, personal computers, fitness trackers, workstations, medical processing devices, and the like. Portable processing devices 302-308 and computers 310-312 may communicate with each other via a direct wired or wireless connections (e.g., Bluetooth, Wifi), or through a local network (e.g., LAN).

In one example, portable processing devices 302, 304 may be communicatively coupled to computer 310 and portable processing devices 306, 308 may be communicatively coupled to computer 312. In this example, computers 310, 312 may be computers from different systems (e.g., 408, 410) and may be physically and/or geographically remote from one another. In some illustrative embodiments, computers 310, 312 may be part of the same system (e.g., 408). Computers 310 and/or 312 may be communicatively coupled to a computer network 402, which may be communicatively coupled to a plurality of servers 314, 316. In the example of FIG. 3, server 314 is communicatively coupled with a plurality of databases 318, 320, 322. The databases may be configured as large-scale databases suitable for use in systems, such as EMRs, EHRs, and the like.

In some illustrative embodiments, system 300 may be configured to distribute mobile intelligent agents among devices (e.g., 302-308) and to the servers (e.g., 314-316). Mobile intelligent agents in the present disclosure are configured as autonomous movable code that are capable of migrating from one device (host) to another carrying data, as well as its state to continue its execution. Mobile agents are advantageous for use in data-driven environments, such as medical systems and have the benefit of possessing numerous desirable qualities, such as autonomy, mobility, adaptive/learning, goal oriented, active/proactive, and being collaborative/communicative. Accordingly, system 300 may benefit from a reduction in network load, improvement in network latency, parallel processing, asynchronous execution, protocol encapsulation, dynamic adaptation, fault-tolerance and robustness. During operation, an agent may be configured to incorporate code, data and context and be transmitted from a portable processing device (e.g., 302-308) and/or computer (e.g., 310-312) to a server (e.g., 314-316). The agent may be configured to carry out one or more function locally on the server, and, after completing the task, the agent may terminate, return back to the client, or migrate to another host to continue execution.

In some illustrative embodiments, the system 300 may be configured on a JADE (Java Agent Development Framework) platform. The JADE platform of system 300 may comprise one or more agent containers configured in a mobile agent module (e.g., 416) that provide an environment where the agents can operate. During operation, a server (e.g., 314, 316) may invoke an Agent Management System (AMS) and the Directory Facilitator (DF) that may be configured within a system agent manager (e.g., 434). The AMS may be configured to manage the entire agent platform while the DF may be configured as a White Pages Service allowing agents to locate other agents.

The agents may be configured with interface with learning modules (e.g., 420) to utilize learning using an Analytic Hierarchy Process (AHP) and/or Case-Based Reasoning (CBR). Unlike conventional techniques that produce a single "correct" decision, AHP is configured to be flexible in allowing users to determine a decision that are specific to their goals and understanding of problems. Additionally, AHP provides a comprehensive and rational framework for structuring decision problems, for representing and quantifying its elements, for relating those elements to overall goals, and for evaluating alternative solutions.

When configuring the AHP platform for system 300, decision problems may be decomposed into a hierarchy of more easily comprehended sub-problems, each of which can be analyzed independently. The elements of the hierarchy can relate to any aspect of the decision problem, and may be configured using exact and/or roughly estimated relations applied to specific decisions. Once the hierarchy is built, the system may systematically evaluate its various elements by comparing them to each other using multiples at a time, with respect to their impact on an element above them in the hierarchy. In making the comparisons, the system 100 can use concrete data about the elements, and also provide evaluation data about the elements' relative meaning and importance. The AHP may convert these evaluations to numerical values that can be processed and compared over the entire range of the problem. A numerical weight or priority may be derived for each element of the hierarchy, allowing diverse and often incommensurable elements to be compared to one another in a rational and consistent way. In a final step of the process, numerical priorities may be calculated for each of the decision alternatives. These numbers represent the alternatives' relative ability to achieve a decision goal, so to allow a straightforward consideration of the various courses of action.

When configured for case-based reasoning (CBR), either instead or, or together with AHP, the system 300 is configured to solve problems by retrieving stored cases/records of similar problems (e.g., via 318-322) that have been solved before and adapting their solutions to fit a new situation. Case-based reasoning may be configured as a multi-step process, where a first step may include a retrieve step, where, given a target problem, the system retrieves from memory (e.g., 318-322) cases relevant to solving it. A case may include a problem, its solution, and, typically, annotations about how the solution was derived. In a reuse step, the system 300 may map the solution from the previous case to the target problem. This may involve adapting the solution as needed to fit the new situation. In a revise step, having mapped the previous solution to the target situation, the system 300 may test the new solution in a simulation and, if necessary, revise. In a retain step, after a solution has been successfully adapted to the target problem, the system 300 may store the resulting experience as a new case in memory (e.g., 318-322).

In some illustrative embodiments, the system 300 may utilize a multi-instance multi-label (MIML) learning framework where a problem may be described by multiple instances and associated with multiple class labels. The MIML framework may be configured with MIMLBoost and MIMLSvm algorithms based on a simple degeneration strategy, which is advantageous for solving problems involving complicated objects with multiple semantic meanings in the MIML framework. In some illustrative embodiments, a KG-MIML-Net model may be used where, instead of depending on previous given representation of instances or labels, an encoder-decoder framework that can jointly learn and update embedding for instances and labels and build mapping between bag of instances and bag of labels. A Recurrent Neural Network (RNN) structure may be utilized as the implementation of both encoder and decoder to better capture high-order dependency among instances and labels. Moreover, a residual-supervised attention mechanism may be embedded to assign weights to instances by their level of importance or severity, including drug potency. Additional knowledge may be extracted including contextual knowledge and structural knowledge. Contextual knowledge in medical data may include, but is not limited to, personal summarization information, such as lab test and demographic. Structural knowledge like instances and labels ontology may be configured as a tree-structure classification scheme such as ICD-9. In some illustrative embodiments, a contextual layer may be added after decoder to combine the personal contextual knowledge. Structural knowledge may be utilized such that that the representation of input instances as a leaf node in tree-structure classification scheme is learned depending on its ancestors. The representation of ancestors may be generated by the mean of their direct children, in some illustrative embodiments. A bidirectional long-short term memory (LSTM) may be used to output the tree-embedding given an instance and the tree-structure classification scheme.

It should be understood by those skilled in the art that the terms "problem" and "solution/decision" as used herein should not be interpreted in the abstract. Instead, these terms refer to a baseline dataset having a plurality of data points (problem), entered into the system and subjected to processing (e.g., via processors 410, 428) in order to produce a processed output, based on any of the learning models discussed above.

Figure 4:
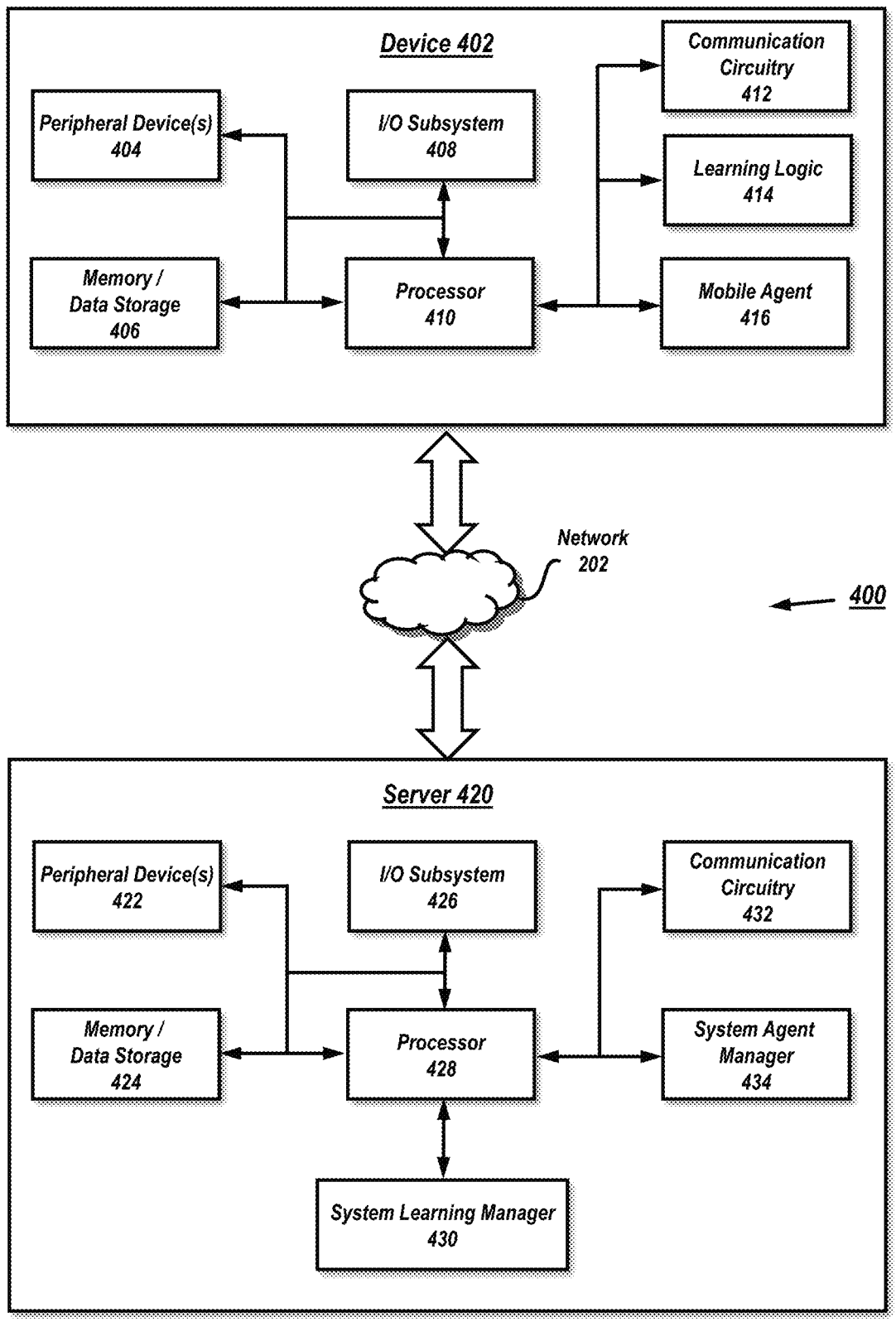
FIG. 4 shows an operating environment for a device and a server in a mobile agent environment for processing medical data under an illustrative embodiment.

FIG. 4 shows an operating environment 400 for system 300 that includes a processing device 402, which may be configured as any of devices 102-108 and/or 108-110, and a server 420, which may be configured as server 114, 116, communicating via the network 112 wherein the operating environment is configured to process medical data including prescription drug data, as explained in greater detail below. In the illustrative embodiment, the processing device 402 includes a processor 410 or processor circuit, one or more peripheral devices 404, memory/data storage 406, communication circuitry 412, input/output (I/O) subsystem, a learning logic module and 414 and mobile agent module 416.

The mobile agent module 416 of environment 200 may be configured to perform functions pertaining to a mobile agent platform, as discussed above. Learning logic module 414 may be configured to perform aspects of data intelligence processing, including, but not limited to AHP, CBR and MIML, discussed above. In some illustrative embodiments, mobile agent module 416 and/or leaning module 414 may be incorporated into memory/data storage 406 with or without a secure memory area, or may be a dedicated component, or incorporated into the processor 410. Of course, processing device 402 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 406, or portions thereof, may be incorporated in the processor 410 in some embodiments.

The processor 410 may be embodied as any type of processor currently known or developed in the future and capable of performing the functions described herein. For example, the processor 410 may be embodied as a single or multi-core processor(s), digital signal processor, microcontroller, or other processor or processing/controlling circuit. Similarly, memory/data storage 406 may be embodied as any type of volatile or non-volatile memory or data storage currently known or developed in the future and capable of performing the functions described herein. In operation, memory/data storage 406 may store various data and software used during operation of the processing device 410 such as access permissions, access parameter data, operating systems, applications, programs, libraries, and drivers.

Memory/data storage 406 may be communicatively coupled to the processor 410 via an I/O subsystem 408, which may be embodied as circuitry and/or components to facilitate input/output operations with the processor 410, memory/data storage 406, and other components of the processing device 402. For example, the I/O subsystem 408 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 408 may form a portion of a system-on-a-chip (SoC) and be incorporated, along with the processor 410, memory/data storage 406, and other components of the processing device 402, on a single integrated circuit chip.

The processing device 402 includes communication circuitry 412 (communication interface) that may include any number of devices and circuitry for enabling communications between processing device 402 and one or more other external electronic devices and/or systems. Similarly, peripheral devices 404 may include any number of additional input/output devices, interface devices, and/or other peripheral devices. The peripheral devices 404 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 420 may be embodied as any suitable server (e.g., a web server, etc.) or similar computing device capable of performing the functions described herein. In the illustrative embodiment of FIG. 2 the server 420 includes a processor 428, an I/O subsystem 426, a memory/data storage 424, communication circuitry 432, and one or more peripheral devices 422. Components of the server 420 may be similar to the corresponding components of the processing device 402, the description of which is applicable to the corresponding components of server 420 and is not repeated herein for the purposes of brevity.

The communication circuitry 432 of the server 420 may include any number of devices and circuitry for enabling communications between the server 420 and the processing device 402. In some embodiments, the server 420 may also include one or more peripheral devices 422. Such peripheral devices 422 may include any number of additional input/output devices, interface devices, and/or other peripheral devices commonly associated with a server or computing device. In some illustrative embodiments, the server 420 also includes system learning manager 430 and system agent manager 434. System agent manager 434 may be configured to invoke an Agent Management System (AMS) and the Directory Facilitator (DF) as discussed above to process and/or transmit mobile agent data provided from device 402. System learning manager 430 may comprise intelligence circuitry and/or modules that communicates via the system (e.g., 300) to learning logic modules (e.g., 414) and perform system-wide processing for AHP, CBR and MIML, discussed above, and may further be configured with a diagnosis module for processing diagnosis data and drug (prescription) data for determining abuse conditions for specific patients.

Continuing with the illustrated embodiment of FIG. 4, communication between the server 420 and the processing device 402 takes place via the network 202 that may be operatively coupled to one or more network switches (not shown). In one embodiment, the network 202 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 402 and the communication circuitry 432 of the server 420 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 202 may include any number of additional devices, such as additional computers, routers, and switches, to facilitate communications between the processing device 402 and the server 420.

The operating environment 400 is configured to identify and predict potential opioid abuse in patients under an illustrative embodiment. In this example, patient identification data, along with associated patient data (e.g., lab test data) and demographic data may be generated and stored in storage (e.g., 406, 424). Patient data may comprise patient condition and/or disease data, such as hypertension, hyperlipidemia, diabetes, back pain, anxiety, obesity, allergic rhinitis, reflux esophagitis, respiratory problems, hypothyroidism, visual refractive errors, general medical exam, osteoarthritis, fibromyalgia/myositis, malaise and fatigue, etc. Additional data may include prescription data and medicine data, including opioid history and opioid-related markers and biomarkers.

System learning manager 430 may be configured to communicate with each learning logic module 414 and centrally instruct or manage data and/or outputs therefrom. In some illustrative embodiments, each learning logic 414 performs all processing locally and provides outputs to system learning manager 420. In some illustrative embodiments, learning logic 414 pre-processes data and transmits the pre-processed data to system learning manger 420 for processing completion. In some illustrative embodiments, system learning manager 430 and learning logic 414 may share processing, depending on the specific application required.

The system learning manager 430 and/or learning logic 414 may also be configured with a diagnosis module that includes code data, diagnosis description data and severity data, relating to a patient's condition and/or characteristics. Such data may be manually inputted or received from a database such as a private and/or public database, as well as medical databases, such as EHRs. The code data may comprise a numerical representation of one or more medical conditions (e.g., ICD-10-CM codes), where the diagnosis description data may comprise a description of the medical condition. The severity data may comprise a numerical representation of the severity of the medical condition. In some illustrative embodiments, a drug classification module in learning logic 414 and/or system learning manager 420 may be configured under an Anatomical Therapeutic Chemical (ATC) classification system, where drugs may be divided into different groups according to the organ or system on which they act and according to their chemical, pharmacological and therapeutic properties. In this example, the drugs may be classified in groups of a plurality (e.g. five) of different levels, where drugs are divided into 14 main groups (first level), with two therapeutic/pharmacological subgroups (second and third levels). A fourth level may be a therapeutic/pharmacological/chemical subgroup and a fifth level may be the chemical substance. The second, third and fourth levels are often used to identify pharmacological subgroups when these are considered to be more appropriate than therapeutic or chemical subgroups. This data may then be processed in learning module 420 (and/or system learning manager 420), which may use any of the techniques described herein to process and calculate/predict actual and/or potential opioid abuse condition(s) for a patient.

To predictively process data and to address data skewness in both instance space and label space, learning logic 414 (and/or system learning manager 420) may utilize machine learning techniques to process complicated objects derived from data having multiple semantic meanings. In cases where complicated objects derived from the data have multiple semantic meanings, learning logic 414 (and/or system learning manager 420) may be configured model high-order dependency and assume the representation of instances or labels to learn robust representation and build complex dependencies. Here, deep learning models, such as KG-MIML-Net may be utilized, where, instead of depending on previous given representation of instances or labels, an encoder-decoder framework may be used to jointly learn and update embedding for instances and labels and build mapping between bag of instances and bag of labels. An RNN structure may be utilized as an implementation of both encoder and decoder to better capture high-order dependency among instances and labels. Moreover, a residual-supervised attention mechanism may be embedded in, learning logic 414 (and/or system learning manager 420) to assign weights to instances by their importance.

In some illustrative embodiments, the weights may be represented by severity data, indicating the severity of a patient condition and/or characteristic, and/or prescription data. Additional knowledge may also by extracted in, learning logic 414 (and/or system learning manager 420) including contextual knowledge data and structural knowledge data, where contextual knowledge data may be derived from the patient data and/or lab test and demographic data. Structural knowledge data may be configured as an instance and/or label ontology configured as a tree-structure classification scheme (e.g., ICD-10-CM) for the data. The contextual layer of, learning logic 414 (and/or system learning manager 420) may be configured to be after the decoder to combine the personal contextual knowledge data, and structural knowledge data may be utilized such that the representation of input instances as the leaf node the in tree-structure classification scheme is learned depending on its ancestors. The representation of ancestors may be generated by the mean of their direct children. A Bi-LSTM may output the tree-embedding given an instance and the tree-structure classification scheme. Under the configuration of FIG. 4, patient data and related medical data may be processed in the system (e.g., 200, 300) in order to calculate actual and/or potential opioid abuse condition(s).

Figure 5:
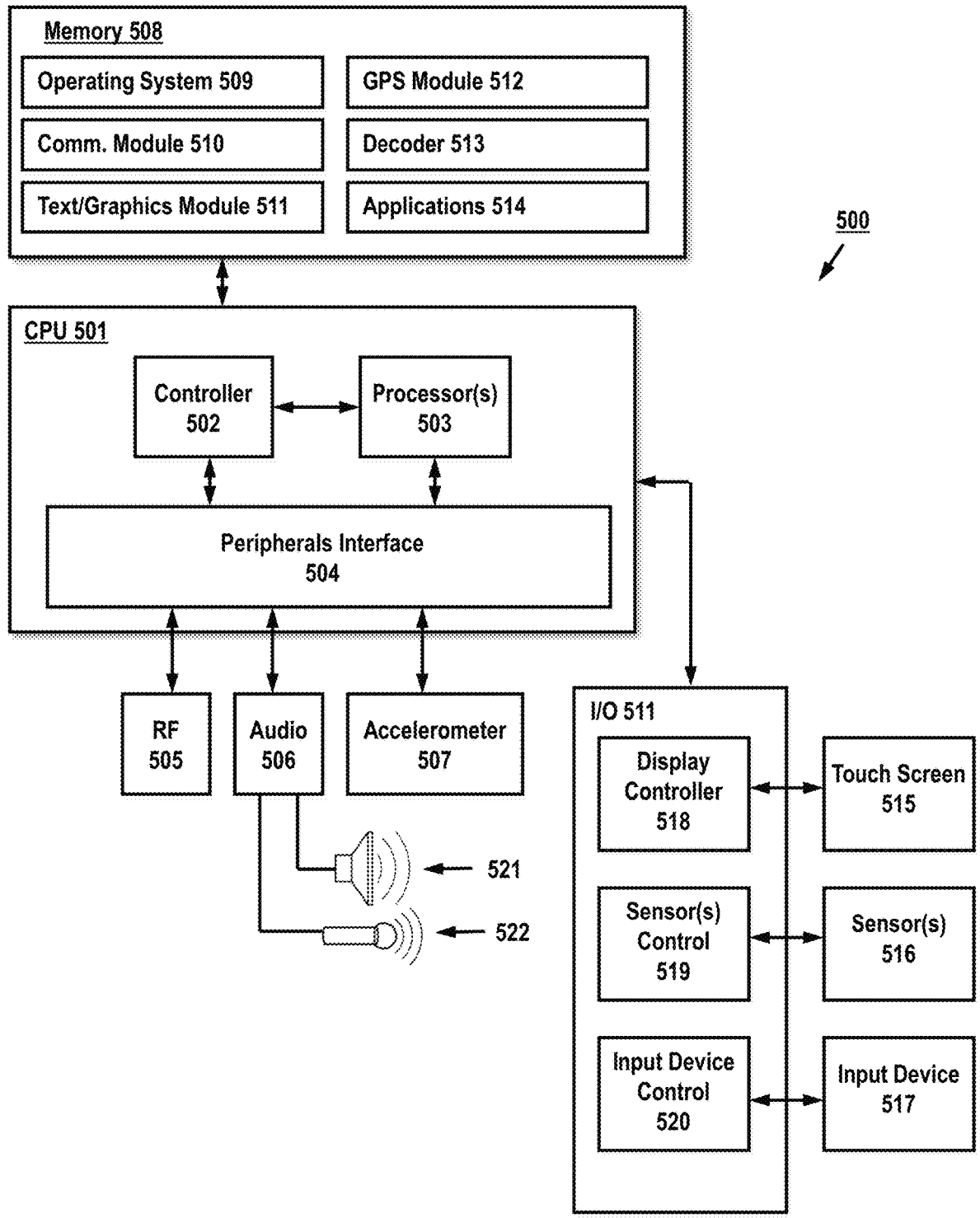
FIG. 5 schematically illustrates an operating environment for a processing device configured to perform medical data processing under an illustrative embodiment.

FIG. 5 is an exemplary embodiment of a computing device 500 (such as processing devices 302. 310), and may be a personal computer, smart phone, tablet computer, laptop and the like. Device 500 may include a central processing unit (CPU) 501 (which may include one or more computer readable storage mediums), a memory controller 502, one or more processors 503, a peripherals interface 504, RF circuitry 505, audio circuitry 506, accelerometer 507, speaker 521, microphone 522, and input/output (I/O) subsystem 221 having display controller 518, control circuitry for one or more sensors 519 and input device control 520. These components may communicate over one or more communication buses or signal lines in device 500. It should be appreciated that device 500 is only one example of a portable multifunction device, and that device 500 may have more or fewer components than shown, may combine two or more components, or a may have a different configuration or arrangement of the components. The various components shown in FIG. 5 may be implemented in hardware or a combination of hardware and software, including one or more signal processing and/or application specific integrated circuits.

Memory (or storage) 508 may include high-speed random access memory (RAM) and may also include non-volatile memory, such as one or more magnetic disk storage devices, flash memory devices, or other non-volatile solid-state memory devices. Access to memory 508 by other components of the device 500, such as processor 503, and peripherals interface 504, may be controlled by the memory controller 502. Peripherals interface 504 couples the input and output peripherals of the device to the processor 503 and memory 508. The one or more processors 503 run or execute various software programs and/or sets of instructions stored in memory 508 to perform various functions for the device 500 and to process data. In some embodiments, the peripherals interface 504, processor(s) 503, decoder 513 and memory controller 502 may be implemented on a single chip, such as a chip 501. In other embodiments, they may be implemented on separate chips.

RF (radio frequency) circuitry 505 receives and sends RF signals, also known as electromagnetic signals. The RF circuitry 505 converts electrical signals to/from electromagnetic signals and communicates with communications networks and other communications devices via the electromagnetic signals. The RF circuitry 505 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 505 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 506, speaker 521, and microphone 522 provide an audio interface between a user and the device 500. Audio circuitry 506 may receive audio data from the peripherals interface 504, converts the audio data to an electrical signal, and transmits the electrical signal to speaker 521. The speaker 521 converts the electrical signal to human-audible sound waves. Audio circuitry 506 also receives electrical signals converted by the microphone 521 from sound waves, which may include utterances from a speaker. The audio circuitry 506 converts the electrical signal to audio data and transmits the audio data to the peripherals interface 504 for processing. Audio data may be retrieved from and/or transmitted to memory 508 and/or the RF circuitry 505 by peripherals interface 504. In some embodiments, audio circuitry 506 also includes a headset jack for providing an interface between the audio circuitry 506 and removable audio input/output peripherals, such as output-only headphones or a headset with both output (e.g., a headphone for one or both ears) and input (e.g., a microphone).

I/O subsystem 511 couples input/output peripherals on the device 500, such as touch screen 515, sensors 516 and other input/control devices 517, to the peripherals interface 504. The I/O subsystem 221 may include a display controller 518, sensor controllers 519, and one or more input controllers 520 for other input or control devices. The one or more input controllers 520 receive/send electrical signals from/to other input or control devices 517. The other input/control devices 517 may include physical buttons (e.g., push buttons, rocker buttons, etc.), dials, slider switches, joysticks, click wheels, and so forth. In some alternate embodiments, input controller(s) 520 may be coupled to any (or none) of the following: a keyboard, infrared port, USB port, and a pointer device such as a mouse, an up/down button for volume control of the speaker 521 and/or the microphone 522. Touch screen 515 may also be used to implement virtual or soft buttons and one or more soft keyboards.

Touch screen 515 provides an input interface and an output interface between the device and a user. Display controller 518 receives and/or sends electrical signals from/to the touch screen 515. Touch screen 515 displays visual output to the user. The visual output may include graphics, text, icons, video, and any combination thereof. In some embodiments, some or all of the visual output may correspond to user-interface objects. Touch screen 515 has a touch-sensitive surface, sensor or set of sensors that accepts input from the user based on haptic and/or tactile contact. Touch screen 515 and display controller 518 (along with any associated modules and/or sets of instructions in memory 508) detect contact (and any movement or breaking of the contact) on the touch screen 515 and converts the detected contact into interaction with user-interface objects (e.g., one or more soft keys, icons, web pages or images) that are displayed on the touch screen. In an exemplary embodiment, a point of contact between a touch screen 515 and the user corresponds to a finger of the user. Touch screen 515 may use LCD (liquid crystal display) technology, or LPD (light emitting polymer display) technology, although other display technologies may be used in other embodiments. Touch screen 515 and display controller 518 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 515.

Device 500 may also include one or more sensors 516 that may include a biometric capture device. Sensors 516 may also include additional sensors, such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 515. Device 500 may also include one or more accelerometers 507, which may be operatively coupled to peripherals interface 504. Alternately, the accelerometer 507 may be coupled to an input controller 520 in the I/O subsystem 221. The accelerometer is preferably configured to output accelerometer data in the x, y, and z axes.

In some illustrative embodiments, the software components stored in memory 508 may include an operating system 509, a communication module 510, a text/graphics module 511, a Global Positioning System (GPS) module 512, decoder 513 and applications 514. Operating system 509 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 510 facilitates communication with other devices over one or more external ports and also includes various software components for handling data received by the RF circuitry 505. An external port (e.g., Universal Serial Bus (USB), Firewire, etc.) may be provided and adapted for coupling directly to other devices or indirectly over a network (e.g., the Internet, wireless LAN, etc.).

Text/graphics module 511 includes various known software components for rendering and displaying graphics on the touch screen 515, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 512 determines the location of the device and provides this information for use in various applications. Applications 514 may include various modules, including health monitoring software, sensor software, navigation software, mapping, address books/contact list, email, instant messaging, and the like. In some illustrative embodiments, Applications 514 may communicate with sensors 516, configured as a biometric capture device.

During operation, an electronic prescription application (e.g., ePrescribe), which may be incorporated with a medical software application, operating on a computer system may be configured to allow devices (e.g., 302-312) to request/receive medical data, including PDMP data, from a server (e.g., 318-322) associated with a PDMP system. In some illustrative embodiments, a back-end configuration may be implemented, where a server (e.g., 420) performs predictive processing on medical data/PDMP data to predict potential abuse conditions for patients. In addition, other medical data, such as fitness tracker data, may provide physiological data that indicates a physiological state of a patient that may be combined with processed PDMP data to determine an abuse condition. Under a simplified example, a server (e.g., 314, 316) may process medical data (e.g., medical history, prescription history, fitness tracker data, etc.) along with PDMP data to establish a score based on the available data. The score may be based on a point system, where If the score meets or exceeds a certain threshold, the server may transmit a mobile agent that may be distributed to devices indicating an actual or abuse condition.

Under the present disclosure, and under a simplified example, a medical software application (e.g., ePrescribe, PainCAS) may be configured to provide notifications to a provider when a possible suspicious activity is discovered. For example, when a patient's eligibility request and medical history status request is processed, and patient history results are scanned and indicates an opioid that was not prescribed by the current provider, a suspicion record is created and transmitted to notify the prescriber. A backend database (e.g., 314, 316) schema/content on the medical software application may map the opioid against possible medical conditions that can be a cause for abuse. A lookup may be performed against this table when patient is being diagnosed for one or more of such symptoms to create a suspicion record and generate/transmit a real time notification for the provider. Continuing with the simplified example, the patient's medical data (including prescription data) may be aggregated into a PDMP score. The medical software application accesses the backend database to search histories of prior PDMP scores for the patient. A trend analysis may be calculated and if the PDMP score shows a characteristic or trend that is at or above a predetermined threshold, a notification is generated and transmitted.

Furthermore medical data in the back-end database (e.g., 314, 316) may be processed for medical conditions/symptoms to produce the PDMP score and/or determine potential opioid abuse. The processing may include mapping of symptoms for determining PDMP scores. In some illustrative embodiments, computer system resources may be conserved by layering medical data processing, in order to limit the amount of processing performed to circumstances where patient characteristics warrant it. For example, a first layer of processing may involve the processing of prescription medical data to generate a first PDMP score for a patient. If the first score is within a predetermined range, or meets or exceeds a threshold, the system (e.g., 300) processes medical history medical data to generate a second PDMP score. If the second score is within a predetermined range, or meets or exceeds a threshold, the system processes medical conditions/symptoms to generate a third PDMP score.

If the third PDMP score is within a predetermined range, or meets or exceeds a threshold, the system may transmit a notification that indicates the patient is an opioid abuse risk. Alternately or in addition, the system may aggregate the plurality of PDMP scores to form a composite PDMP score, whose value may be used to determine if a notification should be transmitted. Those skilled in the art will recognize that the layered PDMP scoring may be configured in a multitude of ways, and may include additional scoring layers, or fewer. The PDMP scoring in the simplified example may comprise assigning values and, in some cases, weights to medical data items and applying a mathematical function (e.g., sum, average, etc.) to the values to establish the score.

In some illustrative embodiments, predictive models may be used as described herein, where scoring comprises applying a predictive model to a set of data. The predictive model may comprise regression, clustering, tree, and neural network models. Once a model has been built, (e.g., XML file) the model specifications can be saved in a file containing all of the information necessary to reconstruct the model. The model file may then be used to generate predictive scores in other datasets. In this example, scoring operates as a transformation of the medical data. The model may be expressed internally as a set of numeric transformations to be applied to a given set of fields (variables) as the predictors specified in the model in order to obtain a predicted result. The scoring process may comprise a plurality of steps. First, the model is built and the model file is saved. The model is built utilizing a dataset for the medical data for which the outcome of interest (or "target") is known. For example, a model may be built predicting potential opioid abusers by utilizing datasets of medical data pertaining to patients having diagnosed opioid abuse and/or dependency. In some embodiments, there need not be a target outcome of interest, for example, when clustering models, or nearest neighbor models are used. Once built, the model is applied to each dataset for each patient to obtain predicted outcomes.

Turning to FIG. 6, a simplified medical data arrangement 600 is shown, comprising PDMP data configured for data mapping and for use in predictive data processing under an illustrative embodiment. While the illustrative arrangement 600 is shown in tabular format, those skilled in the art will recognize that other formats are contemplated in the present disclosure. In the simplified example, medical data arrangement 600 comprises a plurality of data categories, including, but not limited to, an opioid identification value 602, opioid name 604, a symptoms list 606, duration of medication 608 and patient characteristics 610.

In some illustrative embodiments, some or all of the medical data characteristics (e.g., 602-610) are assigned values and stored in a database (e.g., 314, 316). These values may be numerical values, and may alternately or in addition comprise logical operators. Furthermore, patient medical data (e.g., patient medical history, prescription history, etc.) is similarly assigned values. During operation, the medical data and patient medical data is processed to determine an initial patient score. In addition, the medical data and patient medical data is processed through a predictive model to determine a probability that a patient will likely abuse opioids. If, as described above, the processing determines an actual and/or predictive abuse state, the system generates a mobile agent notification that is transmitted to the computer system. As the mobile agent moves through the system, the mobile agent duplicates itself on a device, saves its own state and transmits the saved state to a new host and resumes execution from the saved state. In some illustrative embodiments, the mobile agent notifications are active in that they can choose to migrate between computers at any time during their execution. This makes them a powerful tool for implementing distributed applications in a computer network. The mobile agents may be configured with a static migration path or a dynamic migration path. In some illustrative embodiments, the mobile agent notification may be configured under an open multi-agent systems (MAS) in which agents, that are owned by a variety of stakeholders, continuously enter and leave the system.

FIG. 7 shows a simplified processing identification file 700 that identifies controlled drugs with a patient ID under an illustrative embodiment. In this example, the identification file 700 may be appended to the mobile agent notification file to identify the specific patient and opioid(s) to which an abuse/dependency condition has been calculated. In this simplified example, an opioid ID value 702 is provided, along with a patient ID 704 and patient name 706. In some illustrative embodiments, the patient name 706 may be encrypted using a public/private key so that only devices carrying the private key may decrypt and access the patient name.

Figure 8:
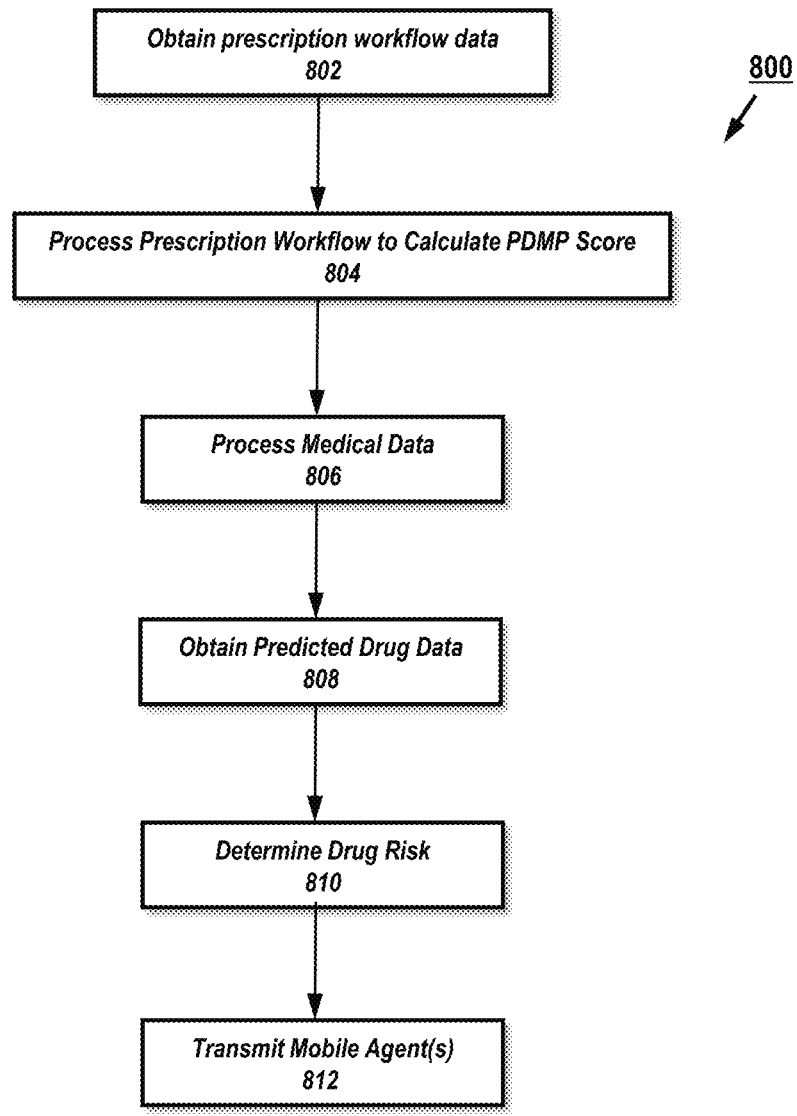
FIG. 8 shows a process for processing medical data comprising prescription data for predictive processing to determine drug risks and to transmit mobile agents under an illustrative embodiment.

FIG. 8 shows a process 800 for processing medical data comprising patient data and prescription data for predictive processing to determine drug risks and to transmit mobile agents under an illustrative embodiment. In block 802, the system (e.g., 300) obtains prescription workflow data, including, but not limited to, prescription data/history, medical data, medical history, etc. as described above. Additionally, the prescription workflow data in block 802 may include corresponding data that pertains to a general population, which may be further organized according to demographics and/or geographic characteristic. In block 804, the system then processes the workflow data to calculate a PDMP score for one or more patients. In block 806 the system processes patient medical data, and in block 808, the system calculates predictive data indicating a statistical likelihood (risk) that a patient will abuse opioids. In block 810, the system determines if the processed data is within a predetermined range or threshold and determines the predictive level of drug risk, and, if a risk is present, transmits one or more notifications via mobile agents in block 812.

Under the various embodiments disclosed herein, the predictive processing provides a computational advantage over conventional systems utilizing medical platforms (e.g., ePrescribe), since the predictive technology allows a system to make determinations requiring less input from the one or more computers, which in turn frees up network resources for other data. In addition, the mobile agent technology allows for data to be communicated throughout the system, providing efficiencies described in greater detail above.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. It is understood by those skilled in the art that the present disclosure do The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A system for processing drug data in a computer network, comprising:
a processor;
a memory, operatively coupled to the processor;
a communications interface, operatively coupled to the processor, wherein the communications interface is configured to
communicate with an electronic prescription application to receive prescription drug monitoring program (PDMP) data from the computer network, and
receive autonomous movable code from the computer network, the autonomous movable code being configured to migrate data states for execution from one device to another, the autonomous moveable code comprising at least one of patient data, lab test data, demographic data, and diagnosis data;
a system agent manager, configured to execute the autonomous movable code; and
a learning logic, configured to process the executed autonomous movable code and the PDMP data and, based on the processing, predictively determine if an opioid abuse condition exists,
wherein the system agent manager is configured to generate new autonomous movable code comprising information on the opioid abuse condition and transmit the new autonomous movable code to the computer network via the communications interface.

2. The system of claim 1, wherein the learning logic is configured to calculate a score based on the PDMP data.

3. The system of claim 1, wherein the learning logic is configured to process the executed autonomous movable code by executing a multi-instance multi-label (MIML) learning framework to determine if the opioid abuse condition exists.

4. The system of claim 3, wherein the learning logic is configured to apply one or more weights to data in the MIML learning framework to determine if the opioid abuse condition exists.

5. The system of claim 4, wherein the one or more weights comprise one of a medical severity value and a drug potency value.

6. The system of claim 1, wherein the learning logic is configured to process the executed autonomous movable code to execute an Analytic Hierarchy Process (AHP) to determine if the opioid abuse condition exists.

7. The system of claim 1, wherein the learning logic is configured to process the executed autonomous movable code to execute a Case-Based Reasoning (CBR) platform to determine if the opioid abuse condition exists.

8. The system of claim 1, wherein the system agent manager is configured to invoke an Agent Management System (AMS) and Directory Facilitator (DF) to receive the autonomous movable code from the computer network.

9. A method for processing drug data in a computer network, comprising:
communicating, via a communications interface, with an electronic prescription application to receive prescription drug monitoring program (PDMP) data from the computer network;
receiving, via the communications interface, autonomous movable code from the computer network, the autonomous movable code being configured to migrate data states for execution from one device to another, the autonomous moveable code comprising at least one of patient data, lab test data, demographic data, and diagnosis data;
executing, via a system agent manager, the autonomous movable code; and
processing, via a learning logic, the executed autonomous movable code and the PDMP data and, based on the processing, predictively determining if an opioid abuse condition exists; and
generating, via the system agent manager, new autonomous movable code comprising information on the opioid abuse condition and transmit the new autonomous movable code to the computer network via the communications interface.

10. The method of claim 9, further comprising calculating, via the learning logic, a score based on the PDMP data.

11. The method of claim 9, wherein executing the autonomous movable code comprises executing a multi-instance multi-label (MIML) learning framework to determine if the opioid abuse condition exists.

12. The method of claim 11, further comprising applying, via the learning logic, one or more weights to data in the MIML learning framework to determine if the opioid abuse condition exists.

13. The method of claim 12, wherein the one or more weights comprise one of a medical severity value and a drug potency value.

14. The method of claim 9, further comprising processing, via the learning logic, the executed autonomous movable code to execute an Analytic Hierarchy Process (AHP) to determine if the opioid abuse condition exists.

15. The method of claim 9, further comprising processing, via the learning logic, the executed autonomous movable code to execute a Case-Based Reasoning (CBR) platform to determine if the opioid abuse condition exists.

16. The method of claim 9, further comprising invoking, via the system agent manager, an Agent Management System (AMS) and Directory Facilitator (DF) to receive the autonomous movable code from the computer network.

17. A method for processing drug data in a computer network, comprising:
communicating, via a communications interface, with an electronic prescription application to receive prescription drug monitoring program (PDMP) data from the computer network;
receiving, via the communications interface, autonomous movable code from the computer network by invoking, via a system agent manager, an Agent Management System (AMS) and Directory Facilitator (DF) to receive the autonomous movable code from the computer network, the autonomous movable code being configured to migrate data states for execution from one device to another, the autonomous moveable code comprising at least one of patient data, lab test data, demographic data, and diagnosis data;
executing, via the system agent manager, the autonomous movable code; and
processing, via a learning logic, the executed autonomous movable code and the PDMP data and, based on the processing, predictively determining if an opioid abuse condition exists; and
generating, via the system agent manager, new autonomous movable code comprising information on the opioid abuse condition and transmit the new autonomous movable code to the computer network via the communications interface.

18. The method of claim 17, wherein executing the autonomous movable code comprises executing a multi-instance multi-label (MIML) learning framework to determine if the opioid abuse condition exists.

19. The method of claim 18, further comprising applying, via the learning logic, one or more weights to data in the MIML learning framework to determine if the opioid abuse condition exists.

20. The method of claim 19, wherein the one or more weights comprise one of a medical severity value and a drug potency value.

* * * * *